United States Patent
Ledoussal et al.

(12) 
(10) Patent No.: US 6,348,624 B1
(45) Date of Patent: *Feb. 19, 2002

(54) PROCESS FOR MAKING CERTAIN BENZOIC ACID COMPOUNDS

(75) Inventors: Benoit Ledoussal, Mason, OH (US); Xiaomin Sharon Zheng, Norcross, GA (US); Ji-In Kim Almstead; Jeffrey Lyle Gray, both of Loveland, OH (US)

(73) Assignee: The Procter & Gamble Co., Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 92 days.

(21) Appl. No.: 09/213,546

(22) Filed: Dec. 17, 1998

Related U.S. Application Data
(60) Provisional application No. 60/070,866, filed on Jan. 9, 1998.

(51) Int. Cl.$^7$ .............................................. C07C 63/337
(52) U.S. Cl. ........................ 562/4.05; 562/423; 562/493
(58) Field of Search ................................ 562/493, 423, 562/405

(56) References Cited

PUBLICATIONS

Sanchez et al., "Quilnolone Antibacterial Agents. Synthesis and Structure–Activity Relationships of 8–Substituted Quinolone–3–carboxylic Acids and 1,8–Naphthyridine–3–carboxylic Acids", *J. Med. Chem.*, 31 (1988) pp. 983–991.

Hagen et al., "Synthesis of 5–Methyl–4–oxo–quinolinecarboxylic Acids", *J. Heterocyclic Chem.*, 27 (1990) pp. 1609–1616.

Bridges et al., "A dramatic Solvent Effect during Aromatic Halogen–Metal Exchanges. Different Products from Lithiation of Polyfluorobromobenzenes in Ether and THF", *J. Org. Chem.*, 55 (1990) pp. 773–775.

Coe et al., "The Lithiation of Fluorinated Benzenes and Its Dependence on Solvent and Temperature", *J. Chem. Soc. Perkin Trans. I.*, (1995) pp. 2729–2737.

Renau et al., "The Synthesis of 3–Bromo–2,4,5–trifluorobenzoic Acid and its Conversion to 8–Bromoquinolonecarboxylic Acids", *J. Heterocyclic Chem.* 33 (1996) pp. 1407–1411.

Moyroud et al., "Lithiations Ortho–dirigees par la Fonction Acide Carboxylique et par les Atomes de Fluor et de Chlore. II. Synthese Regioselective D'Acides Benzoiques et d'Acetophenones Polysubstitutes", *Bull Soc Chem Fr.* 133 (1996) pp. 133–141.

*Primary Examiner*—Paul J. Killos
*Assistant Examiner*—Taylor V. Oh
(74) *Attorney, Agent, or Firm*—David V. Upite; Carl J. Roof

(57) ABSTRACT

The subject invention involves processes for making 2,4-difluoro-3-Q1-benzoic acid, wherein Q1 is derived from an electrophilic reagent, comprising the steps of: (a) treating 1-bromo-2,4-difluorobenzene with a strong, non-nucleophilic base; then treating with an electrophilic reagent which provides Q1, or a functional moiety which is then transformed to Q1, producing 1-bromo-2,4-difluoro-3-Q1-benzene; (b) treating the 1-bromo-2,4-difluoro-3-Q1-benzene with an alkali or alkaline earth metal or organometallic reagent; then treating with carbon dioxide, or with a formylating agent followed by oxidation, to produce 2,4-difluoro-3-Q1-benzoic acid.

The subject invention also involves optional additional steps to further modify Q1, or to substitute a non-hydrogen moiety at the 5-position, at the 6-position, or at both, of the phenyl ring of the 2,4-difluoro-3-Q1-benzoic acid.

14 Claims, No Drawings

PROCESS FOR MAKING CERTAIN BENZOIC ACID COMPOUNDS

CROSS REFERENCE

This application claims priority under Title 35, United States Code 119(e) from Provisional Application Serial No. 60/070,866, filed Jan. 9, 1998.

FIELD OF THE INVENTION

The subject invention relates to processes for making benzoic acid compounds having certain substituents.

BACKGROUND

Benzoic acid compounds having certain substituents are useful as intermediates in processes for making other compounds, including antimicrobial quinolone compounds, and the like.

SUMMARY OF THE INVENTION

The subject invention involves processes for making 2,4-difluoro-3-Q1-benzoic acid:

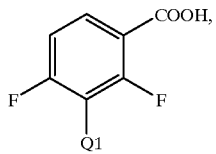

wherein Q1 is derived from an electrophilic reagent, comprising the steps of:

(a) treating 1-bromo-2,4-difluorobenzene:

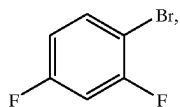

with a strong, non-nucleophilic base; then treating with an electrophilic reagent which provides Q1, or a functional moiety which is then transformed to Q1, producing 1-bromo-2,4-difluoro-3-Q1-benzene:

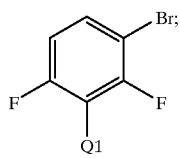

(b) treating the 1-bromo-2,4-difluoro-3-Q1-benzene with an alkali or alkaline earth metal or organometallic reagent; then treating with carbon dioxide, or with a formylating agent followed by oxidation, to produce 2,4-difluoro-3-Q1-benzoic acid.

The subject invention also involves optional additional steps to substitute a non-hydrogen moiety for one or both of the hydrogens attached to the phenyl ring of the 2,4-difluoro-3-Q1-benzoic acid, thus producing:

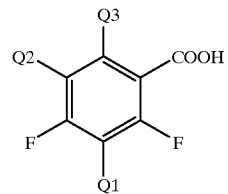

DESCRIPTION OF THE INVENTION

Glossary of Terms

Unless otherwise specified, the following terms have the indicated meanings when used in this application.

"Alkanyl" is an unsubstituted or substituted, linear or branched, saturated hydrocarbon chain radical having from 1 to about 8 carbon atoms, preferably from 1 to about 4 carbon atoms. Preferred alkanyl groups include methyl, ethyl, propyl, isopropyl, and butyl.

"Alkenyl" is an unsubstituted or substituted, linear or branched, hydrocarbon chain radical having from 2 to about 8 carbon atoms, preferably from 2 to about 4 carbon atoms, and having at least one carbon-carbon double bond.

"Alkynyl" is an unsubstituted or substituted, linear or branched, hydrocarbon chain radical having from 2 to about 8 carbon atoms, preferably from 2 to about 4 carbon atoms, and having at least one carbon-carbon triple bond.

"Alkyl" includes alkanyl, alkenyl, alkynyl, and cycloalkyl as defined herein, unless specifically or necessarily structurally limited otherwise or by other restrictions. Alkyl retains this meaning when it is used as part of another word; examples are provided below (e.g., alkylene, haloalkyl). In such words, alkyl can be replaced by any of alkanyl, alkenyl, or alkynyl to narrow the meaning of such words accordingly. Also, as referred to herein, a "lower" alkyl is a hydrocarbon chain comprised of 1 to about 4, preferably from 1 to about 2, carbon atoms. Preferred alkyl are alkanyl or alkenyl; more preferred is alkanyl.

"Alkylene" is a hydrocarbon diradical. Preferred alkylene includes ethylene and methylene.

"Heteroatom" is a nitrogen, sulfur or oxygen atom. Groups containing one or more heteroatoms may contain different heteroatoms.

"Heteroalkyl" is an unsubstituted or substituted chain radical having from 2 to about 8 members comprising carbon atoms and at least one heteroatom.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to about 9 carbon atoms, preferably 3 to about 6 carbon atoms. Polycyclic rings contain from 7 to about 17 carbon atoms, preferably from 7 to about 13 carbon atoms.

"Cycloalkyl" is a saturated or unsaturated, but not aromatic, carbocyclic ring radical. Preferred cycloalkyl groups are saturated, and include cyclopropyl, cyclobutyl and cyclopentyl, especially cyclopropyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to about 9 carbon and heteroatoms, preferably 3 to about 6 carbon and heteroatoms. Polycyclic rings contain from 7 to about 17 carbon and heteroatoms, preferably from 7 to about 13 carbon and heteroatoms.

"Aryl" is an unsubstituted or substituted aromatic carbocyclic ring radical. Preferred aryl groups include phenyl, 2,4-difluorophenyl, 4-hydroxyphenyl, tolyl, xylyl, cumenyl and naphthyl. Preferred substituents for aryl include fluoro and hydroxy.

"Heteroaryl" is an unsubstituted or substituted aromatic heterocyclic ring radical. Preferred heteroaryl groups include thienyl, furyl, pyrrolyl, pyridinyl, pyrazinyl, thiazolyl, quinolinyl, pyrimidinyl and tetrazolyl.

"Alkoxy" is an oxygen radical having a hydrocarbon chain substituent, where the hydrocarbon chain is an alkyl (i.e., —O-alkyl or —O-alkanyl). Preferred alkoxy groups are saturated, and include methoxy, ethoxy, propoxy and allyloxy.

"Acyl" is a radical formed by removal of the hydroxy from a carboxylic acid (i.e., R-carbonyl or R—C(O)—). Preferred acyl groups include, for example, acetyl, formyl, and propionyl.

"Halo", "halogen", or "halide" is a chloro, bromo, fluoro or iodo atom radical.

"Optical isomer", "stereoisomer", "diastereomer" as referred to herein have the standard art recognized meanings (Cf., *Hawley's Condensed Chemical Dictionary* 11th Ed.).

Processes for Making Compounds

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2), Fieser & Fieser, *Reagents for Organic Synthesis* (16 volumes), L. Paquette, *Encyclopedia of Reagents for Organic Synthesis* (8 volumes), Frost & Fleming, *Comprehensive Organic Synthesis* (9 volumes) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The starting material for the subject invention processes is 1-bromo-2,4-difluorobenzene:

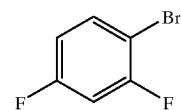

(1)

A first step of the subject processes is to provide a non-hydrogen moiety (Q1) in the 3-position of the starting material to produce 1-bromo-2,4-difluoro-3-Q1-benzene:

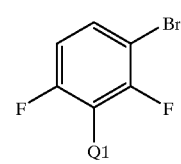

(2)

The 1-bromo-2,4-difluorobenzene is treated with a strong, non-nucleophilic base, typically in an aprotic solvent. This base may be any base useful in permutational hydrogen-metal exchange. Preferred bases include lithium diisopropylamide (LDA), lithium 2,2,6,6-tetramethylpiperidide (LiTMP), lithium bis(trimethylsilyl)amide (LTSA), t-butoxide, or other known bases for this purpose. Suitable bases are known in the literature, and can be found in common reference texts as non-nucleophilic bases. Most preferred is LDA, which produces intermediates that are reasonably stable over a range of times and temperatures. It is preferred that this reaction be carried out at a temperature of above about −80° C. and no more than about 40° C., more preferably no more than about room temperature, most preferably no more than about −40° C. Temperature may vary with the base used; for example, the most preferred reaction temperature is about −65° C. with LDA. Reaction times may be up to about 24 hours, more preferably are about 2 hours. Most preferably the process is carried on as soon as it is apparent that the resulting benzene derivative may proceed to the next step in the process. It is also preferred that this reaction take place under an inert atmosphere.

After the base has reacted with the 1-bromo-2,4-fluorobenzene, an electrophilic reagent provides the desired Q1 substituent or a functional moiety which can be transformed into the desired Q1 substituent. Non-limiting examples of electrophilic reagents and the resulting Q1 substituent are shown in the following table:

TABLE 1

| Q1 | Electrophilic Reagents |
|---|---|
| alkanyl (—R) | R—I, R—Br, ROS(O$_2$)OR, ROSO$_2$R' |
| fluoro (—F) | FClO$_3$ |
| chloro (—Cl) | (CCl$_3$)$_2$, (CCl$_3$)$_2$CO, N-chlorosuccinimide |
| bromo (—Br) | Br$_2$, (CH$_2$Br)$_2$ |
| iodo (—I) | I$_2$, (CH$_2$I)$_2$ |
| hydroxy (—OH) | O$_2$, tBuOOH, BR$_3$/H$_2$O$_2$, (MeO)$_3$B/H$_2$O$_2$ |
| alkanylthio (—SR) | RSSR |
| formyl (—C(O)H) | DMF, HC(O)—NR$_2$ |
| carboxyl (—COOH) | CO$_2$ |
| carboxylate (—COOR) | Cl—COOR |
| hydroxyalkanyl (—CHOHR) | HC(O)R, R$_2$C(O) |

TABLE 1-continued

| Q1 | Electrophilic Reagents |
|---|---|
| aryl (—Ar) | transition metal (e.g., Pd)/Ar—I or Ar—Br |
| alkenyl (—CH=CH—R) | transition metal/R—CH=CHI or R—CH=CHBr |

Typically, the electrophilic reagent is added to the previous reaction mixture while it is still at the temperature indicated above for that reaction. The resulting mixture is allowed to warm under ambient conditions to ambient temperature; this typically takes at least about ten minutes, but no more than about 24 hours, usually no more than about 2 hours. The reaction is complete within that time.

Solvents suitable for these first-step reactions are typically aprotic. Preferably these solvents are compatible with the bases used in the reactions. Preferred solvents include the ethers (e.g., diethylether), glymes, dioxane, and especially tetrahydrofuran (THF). Such solvents are known in the art, and suitable substitutions are made depending on the base, electrophile, and the polarity and solubility characteristics of the reactants and resulting compound.

Other Q1 moieties can be derived from those in the above table by using additional reaction steps well-known to the skilled chemist. Non-limniting examples include alkoxy or acyloxy Q1 moieties derived from the hydroxy; alkenyl, hydroxyalkyl, and aminoalkyl moieties derived from the formyl; and trifluoroalkyl, amide, and imidazoyl moieties derived from the carboxyl.

Preferred Q1 moieties include alkanyl, alkenyl, aryl, halo, hydroxy, alkoxy, acyloxy, alkanylthio, formyl, carboxyl, and carboxylate; more preferred are alkanyl, halo, hydroxy, alkoxy, acyloxy, alkanylthio, fornyl, carboxyl, and carboxylate. Still more preferred Q1 moieties include alkanyl, halo, hydroxy, alkoxy, and alkanylthio. Preferred Q1 alkanyl moieties have from 1 to about 2 carbon atoms; methyl is preferred. Preferred Q1 alkenyl moieties have from 2 to about 4 carbon atoms; ethenyl is preferred. All Q1 alkyl moieties are preferably unsubstituted or substituted with from 1 to about 3 fluoro moieties. More preferred Q1 is selected from fluoro, chloro, methyl, methoxy, monofluoromethyl, difluoromethyl, trifluoromethyl, monofluoromethoxy, difluoromethoxy, and trifluoromethoxy. Still more preferred Q1 is selected from methyl, methoxy, and chloro; especially either methoxy or chloro.

The 1-bromo-2,4-difluoro-3-Q1-benzene produced in step 1 above is then optionally purified by conventional purification steps, such as distillation, extraction, chromatography, or a combination thereof, or with other known steps. Distillation is a preferred purification step at this stage in the subject processes.

In a second step of the subject invention processes, the 1-bromo-2,4-difluoro-3-Q1-benzene from the above first step is converted to the corresponding benzoic acid, 2,4-difluoro-3-Q1-benzoic acid:

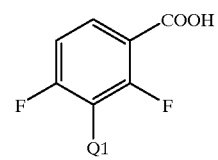

(3)

This benzoic acid is prepared by treating the 1-bromo-2,4-difluoro-3-Q1-benzene compound with an equivalent of an alkali or alkaline earth metal or organometallic reagent useful in permutational halogen-metal exchange, typically in an aprotic solvent (preferably the same solvent as used for the first step). Suitable reagents are known in the literature, and can be found in common reference texts. Preferred strong base reagents include metals such as lithium, sodium, potassium, and magnesium; and lower alkanyl lithiums, such as methyllithium, ethyllithium, and n-butyllithium. The most preferred strong base for this reaction is n-butyllithium, which produces intermediates that are reasonably stable over a range of times and temperatures. It is preferred that the temperature for this reaction be at least about −800° C. and no more than about 40° C., more preferably no more than about room temperature, most preferably no more than about −40° C. Temperature may vary with the base used; for example, the most preferred reaction temperature is about −70° C. with n-butyllithium. Reaction times may be up to about 24 hours; more preferably are at least about 10 minutes, and no more than about 30 minutes. Most preferably the process is carried on as soon as it is apparent that the resulting intermediate derivative may proceed to the next step in the process. It is also preferred that this reaction take place in an inert atmosphere.

The resulting reaction mixture is then preferably treated with carbon dioxide to produce the target 2,4-difluoro-3-Q1-benzoic acid compound. Alternatively, the reaction mixture is then treated with a formylating agent, such as a formamide, preferably N,N-dirnethylformamide (DMF). These reactions are usually exothermic and proceed rapidly. To prevent side reactions, it is preferred that the temperature be maintained at those indicated in the previous paragraph by cooling the reaction mixture. The time required for this reaction is limited primarily by the cooling capacity of the equipment and procedures used. The carbon dioxide or DMF must be added slowly enough to insure that the reaction mixture does not overheat. If carbon dioxide is used, the resulting benzoic acid compound is useful without farther purification after a typical work up.

If DMF or a similar formylating compound is used, the resulting benzaldehyde compound is oxidized to the corresponding benzoic acid via oxidation. This can be achieved by exposure of the benzaldehyde compound to air, or by using other known oxidizing reagents, such as chromic acid or potassium permanganate. The oxidation reaction is preferably carried out in a non-ether solvent; preferred solvents include halogenated solvents, such as dichloromethane and chloroform, and aromatic solvents, such as benzene and toluene. The oxidation reaction is preferably carried out at about ambient temperature, but may be carried out at temperatures up to the reflux temperature of the solvent. The same resulting benzoic acid compound is used without further purification after a typical work up.

The subject invention also involves processes for making 2,4-difluoro-3-Q1-5-Q2-6-Q3-benzoic acid:

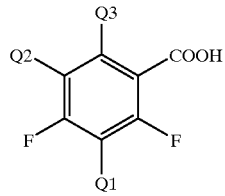

(4)

wherein either or both Q2 and Q3 are moieties other than hydrogen, from the above 2,4-difluoro-3-Q1-benzoic acid (structure (3)).

Preferred Q2 moieties include hydrogen, iodo, bromo, chloro, hydroxy, alkoxy, nitro, amino, alkyl, cyano and acyl. More preferred Q2 include hydrogen, bromo, chloro, hydroxy, alkoxy, amino, alkanyl, alkenyl, and cyano. Still more preferred Q2 include hydrogen, bromo, hydroxy, alkanoxy, alkanyl, and cyano. Alkanyl, alkenyl, and alkanoxy moieties are preferably unsubusituted or substituted with from 1 to about 3 fluoro, or alkanyl and alkenyl may be substituted with one amino or one hydroxy or lower alkoxy. More preferred still Q2 include hydrogen, hydroxy, bromo, unsubstituted methyl, and methyl substituted with from one to three fluoro.

Preferred Q3 moieties include hydrogen, halo, amino, hydroxy, alkoxy, alkyl, alkanylthio, formyl, carboxyl, carboxylate, and aryl. More preferred Q3 include hydrogen, halo, hydroxy, lower alkanoxy, and lower alkanyl.

For the above Q3 moieties, alkanyl and alkanoxy moieties are preferably unsubusituted or substituted with from 1 to about 3 fluoro, or alkanyl may be substituted with one amino or one hydroxy. Still more preferred Q3 include hydrogen, amino, hydroxy, chloro, unsubstituted methyl, and methyl substituted with from one to three fluoro.

In an optional third step of the subject invention processes, the 2-4-difluoro-3-Q1-benzoic acid compound prepared in the above second step is amenable to derivatization of the 5-position, thus producing 5-Q2-2,4-difluoro-3-Q1-benzoic acid. The 5-position is preferentially derivatized before the 6-position; the amount of reactant is preferably limited so that only the 5-position is derivatized. If the same moiety is desired in both the 5- and 6-positions, excess reactant is used in this optional third step, thus producing 5,6-diQ2-2,4-difluoro-3-Q1-benzoic acid.

If derivatization of the 5-position, or both the 5- and 6-positions, is desired, the reactions chosen depend on the desired functionality, for example: Halo:

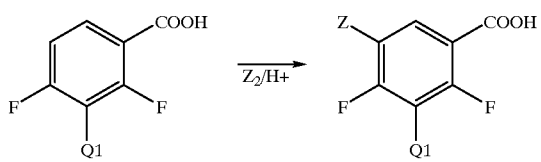

Where Z is a halo, preferably bromo. This reaction occurs under acidic conditions, such as in acetic acid, preferably with a halide activating reagent, such as a silver reagent (e.g., AgNO$_3$). Hydroxy and alkoxy:

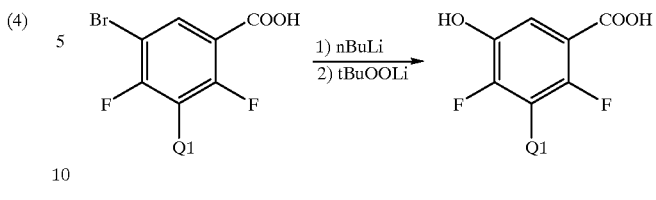

5-Bromo-2-4-difluoro-3-Q1-benzoic acid, made as indicated above, is treated with n-butyllithium, then with lithium t-butyl hydroperoxide to give, after work-up, 5-hydroxy-2-4-difluoro-3-Q1-benzoic acid The corresponding alkoxy compound is readily made by converting the hydroxy moiety to an alkoxy moiety by any known method, e.g. reaction with alkyl iodide or dialkyl sulfate in acetone/water in the presence of base.

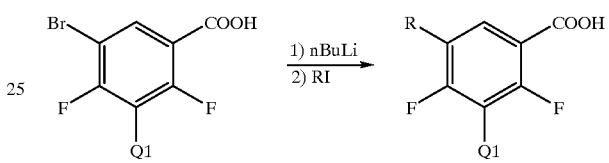

5-Bromo-2,4, difluoro-3-Q1-benzoic acid is treated with n-butyllithium, then with alkanyl (R) iodide to afford 5-alkanyl-2,4-difluoro-3-Q1-benzoic acid.

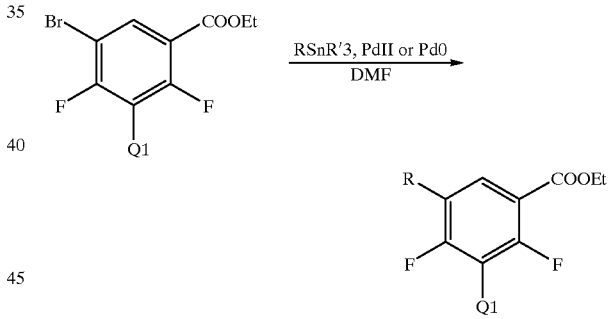

Alternatively, 5-bromo-2,4-difluoro-3-Q1-benzoic acid ethyl ester is treated with R-trialkanyltin, where R is alkanyl (preferably the same as for the trialkanyl), alkenyl or aryl, in presence of palladium II or 0 as catalyst in dimethylformamide to afford 5-alkyl-2,4-difluoro-3-Q1-benzoic acid ethyl ester or 5-aryl-2,4-difluoro-3-Q1-benzoic acid ethyl ester.

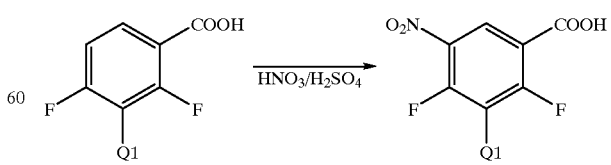

Nitration occurs via treatment with activated nitric acid, such as in a mixture of nitric and sulfuiric acids. Reduction of the nitro moiety to an amino moiety may be performed via any appropriate reduction process. Cyano:

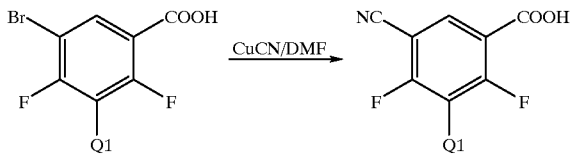

5-Bromo-2,4-difluoro-3-Q1-benzoic acid is treated with copper cyanide in a dipolar aprotic solvent like DMF to afford 5-cyano-2,4-difluoro-3-Q1-benzoic acid.

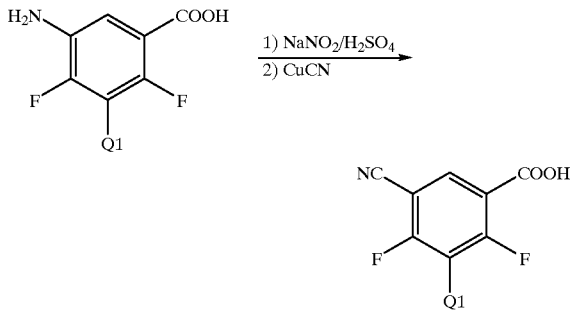

Alternatively, 5-amino-2,4-difluoro-3-Q1-benzoic acid is treated with sodium nitrite in a solution of sulfuric acid. The resulting diazoniunm salt is then treated with copper cyanide to afford 5-cyano-2,4-difluoro-3-Q1-benzoic acid.

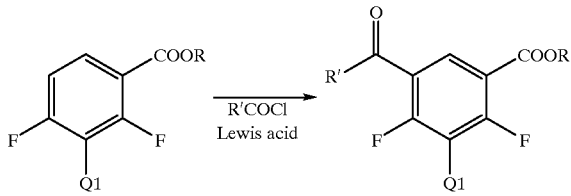

Preparation of acyl compounds is accomplished by introducing an acylating reagent, for example R'COCl (where R' is an alkyl or aryl), preferably in the presence of a Lewis acid, for example $AlCl_3$.

Once the 5-position is derivatized with a Q2 other than hydrogen, the 6-position can be derivatized with a Q3 other than hydrogen, if that is desired. Therefore, in an optional fourth step of the subject invention processes, a non-hydrogen Q3 moiety may be incorporated, thus producing a benzoic acid compound of structure:

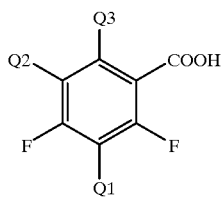

This is preferably eved by using reaction conditions similar to the appropriate immediately preceding methods for Q2, thus achieving the Q3 moiety desired: halo, hydroxy, alkoxy, alkanyl, nitro, amino, cyano, or acyl.

If a non-hydrogen Q3 moiety is desired, while retaining Q2 as hydrogen, a different optional third step of the subject invention processes is used to derivatize the 6-position but not the 5-position, thus producing 6-Q3-2,4-difluoro-3-Q1 benzoic acid.

An example of a preferred method for derivatizing the 6-position but not the 5-position is by using the following scheme:

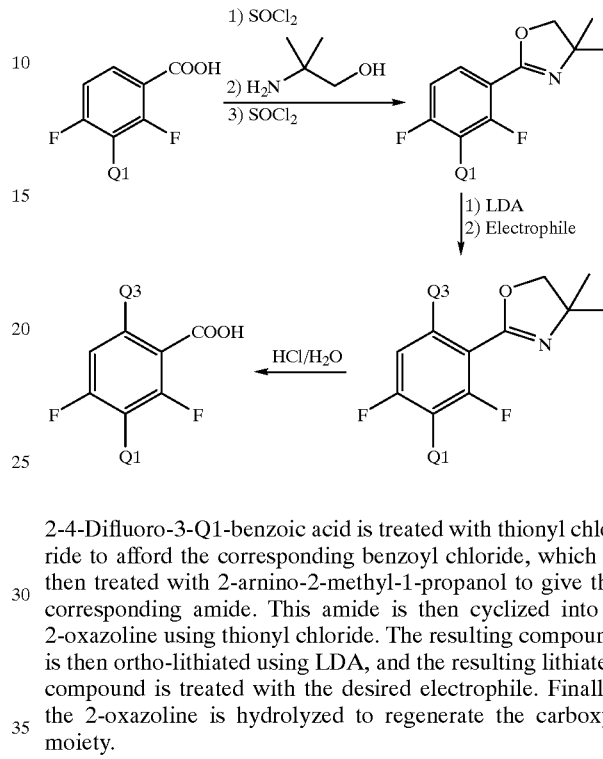

2-4-Difluoro-3-Q1-benzoic acid is treated with thionyl chloride to afford the corresponding benzoyl chloride, which is then treated with 2-arnino-2-methyl-1-propanol to give the corresponding amide. This amide is then cyclized into a 2-oxazoline using thionyl chloride. The resulting compound is then ortho-lithiated using LDA, and the resulting lithiated compound is treated with the desired electrophile. Finally, the 2-oxazoline is hydrolyzed to regenerate the carboxyl moiety.

Preferred electrophiles usefull in the above scheme are those listed in above Table 1, each of which results in Q3 being the moiety listed as Q1 for such electrophile in the table.

For illustration, the following examples of processes for making the benzoic acid compounds are provided; the examples are not meant to be limiting.

EXAMPLE A

3-Chloro-2,4-difluoro-bromobenzene

To a solution of 19 ml (0.135 mole) of diisopropylarnine in 125 ml of tetrahydroflran (TBF) cooled at −20° C. is added 80 ml of n-butyllithium (1.6 M in hexane). The temperature is raised to 0° C. for 5 minutes and lowered to −78° C. Then 25 g (0.129 mole) of 2,4-difluoro-bromobenzene is then added and the reaction is stirred at −65° C. for 2 hours. Then, 25 ml (0.164 mole) of hexachloroacetone is added and the solution is warmed at room temperature. After evaporation of the solvent, the residue is distilled under vacuum to give the desired product.

3-Chloro-2,4-difluorobenzoic acid

To a solution of 21.5 g (0.0945 mole) of 3-chloro-2,4-difluoro-bromobenzene in 220 ml of ether at −78° C. is added 59 ml of 1.6 M n-butyllithium diluted in 60 ml of ether keeping the temperature below −70° C. After 15 minutes, $CO_2$ is bubbled in the reaction keeping the temperature below −70° C. After warming to room temperature, water and hydrochloric acid are added and the organic phase separated, and dried. Removal of the solvent affords the desired product.

EXAMPLE B
3-Methyl-2,4-difluoro-bromobenzene

Diisoproplylamine (11.9 ml, 85 mmol) is dissolved in 50 ml of anhydrous THF and cooled in a dry ice/acetone bath. n-Butyllithium (34 ml of a 2.5 M solution in hexanes, 85 mmol) is added dropwise. After 15 minutes, a solution of 1-bromo-2,4-difluorobenzene (16 g, 83 mmol) in 8 ml of TBF is added at a rate to keep the temperature below −65° C. The reaction is stirred for 2.5 hours then a solution of iodomethane (10.3 ml, 166 mmol) in 8 ml of TBF is added to the reaction. The ice bath is removed and the reaction is allowed to warm to room temperature. After 2 hours the reaction is quenched with water and 1N HCl. The aqueous layer is extracted twice with ether. The combined organics are washed with brine and dried over $Na_2SO_4$. Removal of the solvent affords the desired product.

3-Methyl-2,4-difluorobenzoic acid

3-Methyl-2,4-difluoro-bromobenzene (16.07 g 77.6 mmol) is dissolved in 120 ml anhydrous ether and cooled in a dry ice/acetone bath. A solution of butyllithium (20.5 ml of a 2.5 M solution in hexanes, 76.2 mmol) in 15 ml of ether is added dropwise at a rate to keep the temperature below −65° C. After 45 minutes, $CO_2$ is bubbled through the solution keeping the temperature below −65° C. After the temperature stabilized, $CO_2$ bubbling is continued as the reaction is allowed to warm to room temperature. The mixture is quenched with 30 ml of water and acidified to pH 2 with 1N HCl. The layers are separated and the aqueous layer is extracted with ether. The combined organics are washed with brine and saturated sodium bicarbonate. The bicarbonate layer is then acidified with 1N HCl to pH3. The resulting solid is filtered, washed with water, and dried under vacuum.

EXAMPLE C
3-Hydroxy-2,4-difluoro-bromobenzene

A quantity of 40.2 ml of 2.0 M lithium diisopropylamine (LDA) is dissolved in 80 ml of TIF at −78° C. and 15.4 g of 2,4-difluorobromobenzene is added keeping the temperature below −65° C. The reaction is stirred at −65° C. for 2 hours and 6.6 ml of 6 M anhydrous t-butyl hydroperoxide is added. After warming at room temperature, 100 ml of water is added and the mixture acidified. The solvent is removed by evaporation and the aqueous layer extracted with ether. The extracts are dried and then concentrated to give the desired product.

3-Methoxy-2,4-difluoro-bromobenzene

A quantity of 3.7 g of 3-hydroxy-2,4-difluoro-bromobenzene is dissolved in 25 ml of acetone and 2.5 g of potassium carbonate is added followed by 2.2 ml of methyl iodide. The mixture is stirred at 20° C. for 6 hours and the solvent evaporated. After addition of dichloromethane, the suspension is filtered. Evaporation of the solvent affords the desired product.

3-Methoxy-2,4-difluorobenzoic acid

A procedure analogous to the 3-chloro-2,4-difluorobenzoic acid preparation is used starting from 3-methoxy-2,4-difluoro-bromobenzene.

EXAMPLE D
5-Bromo-3-chloro-2,4-difluorobenzoic acid

In a mixture of 50 ml of acetic acid, 10 ml of water and 13 ml of nitric acid is dissolved 2 g (0.014 mole) of 3-chloro-2,4-difluorobenzoic acid and 3.64 ml (0.028 mole) of bromine. A solution of 3.52 g (0.0208 mole) of silver nitrate in 10 ml of water is then added slowly. After 14 hours at 20° C., the precipitate is filtered and rinsed with ether. The organic phase is washed with sodium bisulfite, then water and dried. Removal of the solvent affords the desired product.

EXAMPLE E
5-Nitro-3-chloro-2,4-difluorobenzoic acid

An amount of 1 g of 3-chloro-2,4-difluorobenzoic acid is added to a mixture of 1 ml of fuming nitric acid and 1.3 ml of sulfuiric acid at 0° C. The suspension is then stirred at room temperature for 30 minutes and poured on ice. Filtration affords the desired product.

EXAMPLE F
Ethyl 5-(1-ethoxvvinyl)-3-chloro-2,4-difluorobenzoate

A flask containing 228 mg of ethyl 5-bromo-3-chloro-2,4-difluorobenzoate, 38 mg of tris(dibenzylideneacetone)dipalladium, and 30 mg of tri-o-tolylphosphine in 4 mL of anhydrous toluene is purged with argon and stirred at room temperature for 20 min. Then 400 uL of tributyl(1-ethoxyvinyl)tin is added neat, and the mixture is heated to 80° C. overnight. The crude product mixture is purified by chromatography to give the desired product as a white solid.

The benzoic compounds made by the subject invention processes can be used to prepare a number of useful compounds, including quinolone compounds by known methods, such as those depicted in the following scheme.

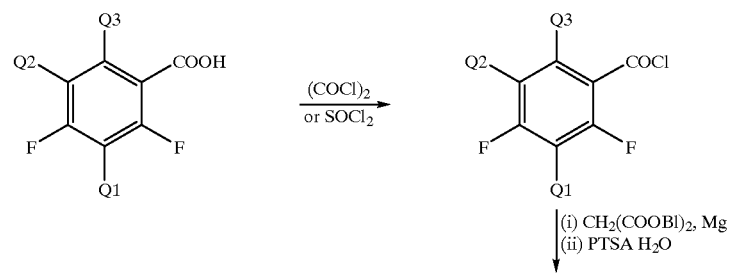

-continued

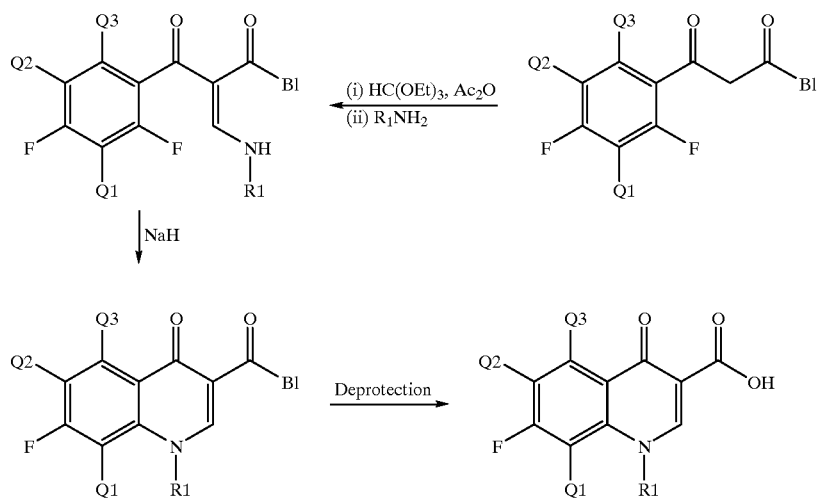

Bl = Blocking group.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A process for making 2,4-difluoro-3-Q1-benzoic acid:

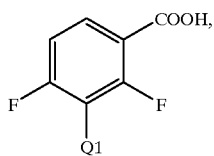

wherein Q1 is derived from an electrophilic reagent, comprising the steps of:

(a) treating 1-bromo-2,4-difluorobenzene:

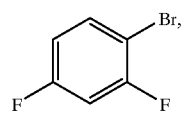

with a strong, non-nucleophilic base; then treating with an electrophilic reagent which provides Q1, or a functional moiety which is then transformed to Q1, producing 1-bromo-2,4-difluoro-3-Q1-benzene:

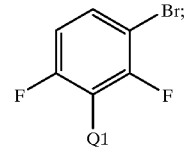

(b) treating the 1-bromo-2,4-difluoro-3-Q1-benzene with an alkali or alkaline earth metal or organometallic reagent; then treating with carbon dioxide, or with a formylating agent followed by oxidation, to produce 2,4-difluoro-3-Q1 -benzoic acid.

2. The process of claim 1 wherein the process optionally includes additional reaction steps which result solely in modification of the Q1 moiety.

3. The process of claim 2 wherein the electrophilic reagent is selected from the group consisting of RI, RBr, ROS(O$_2$)OR, ROSO2R', FClO$_3$, (CCl$_3$)$_2$, (CCl$_3$)$_2$CO, N-chlorosuccinimide, Br$_2$, (CH$_2$Br)$_2$, I$_2$, (CH$_2$I)$_2$, O$_2$, tBuOOH, BR$_3$/H$_2$O$_2$, (MeO)$_3$B/H$_2$O$_2$, RSSR, DMF, HC(O)NR$_2$, CO$_2$, ClCOOR, HC(O)R, R$_2$CO, transition metal/ArI, transition metal/RCH═CHI, wherein R is lower alkanyl and Ar is aryl.

4. The process of claim 3 wherein Q1 of the final compound produced in the process is selected from the group consisting of alkanyl, alkenyl, aryl, halo, hydroxy, alkoxy, acyloxy, alkanylthio, formyl, carboxyl, and carboxylate.

5. The process of claim 4 wherein Q1 is selected from the group consisting of alkanyl, halo, hydroxy, alkoxy, acyloxy, alkanylthio, formyl, carboxyl, and carboxylate.

6. The process of any of claims 1, 3 and 5, wherein step (b) comprises treating the 1-bromo-2,4-difluoro-3-Q1-benzene with a strong base; then treating with carbon dioxide.

7. A process for making 5-Q2-6-Q3-2,4-difluoro-3-Q1-benzoic acid:

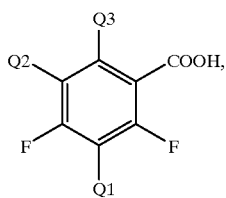

wherein Q1 is derived from an electrophilic reagent, comprising the steps of:

(a) treating 1-bromo-2,4-difluorobenzene:

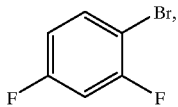

with a strong, non-nucleophilic base; then treating with an electrophilic reagent which provides Q1 or a functional moiety which is then transformed to Q1, producing 1-bromo-2,4-difluoro-3-Q1-benzene:

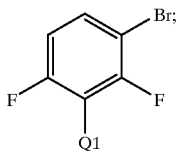

(b) treating the 1-bromo-2,4-difluoro-3-Q1-benzene with an alkali or alkaline earth metal or organometallic reagent; then treating with carbon dioxide, or with a formylating agent followed by oxidation, to produce 2,4-difluoro-3-Q1-benzoic acid;

(c) optionally, further modifying the Q1 moiety with additional reaction steps;

(d) optionally incorporating a non-hydrogen Q2 or Q3 moiety, or the same non-hydrogen moiety as both Q2 and Q3, with additional reaction steps;

(e) if a non-hydrogen Q2 has been incorporated in step (d), optionally incorporating a non-hydrogen Q3 moiety with additional reaction steps.

8. The process of claim 7 wherein step (d) is selected from the group consisting of:

(i) incorporating a halo Q2 by treating the 2,4-difluoro-3-Q1-benzoic acid with $Z_2$ under acidic conditions, where Z is halo;

(ii) incorporating a hydroxy Q2 or alkoxy Q2 by making 5-bromo-2,4-difluoro-3-Q1-benzoic acid as in step (i); then treating the 5-bromo-2,4-difluoro-3-Q1-benzoic acid with n-butyllithium, then with lithium t-butyl hydroperoxide to give the hydroxy Q2; and optionally alkylating the hydroxy Q2 to the alkoxy Q2;

(iii) incorporating an alkanyl, alkenyl or aryl Q2 by making 5-bromo-2,4-difluoro-3-Q1-benzoic acid as in step (i); then treating the 5-bromo-2,4-difluoro-3-Q1-benzoic acid with n-butyllithium, then with alkanyl, alkenyl or aryl iodide to give the alkanyl, alkenyl or aryl Q2; or, alternatively, treating the 5-bromo-2,4-difluoro-3-Q1-benzoic acid with R-trialkanyltin, where R is alkanyl, alkenyl or aryl, in the presence of catalyst to give the alkanyl, alkenyl or aryl Q2;

(iv) incorporating a nitro Q2 or amino Q2 by treating the 2,4-difluoro-3-Q1-benzoic acid with activated nitric acid to give the nitro Q2, and optionally reducing the nitro Q2 to the amino Q2;

(v) incorporating a cyano Q2 by making 5-bromo-2,4-difluoro-3-Q1-benzoic acid as in step (i), then treating the 5-bromo-2,4-difluoro-3-Q1-benzoic acid with a heavy metal cyanide to give the cyano Q2; or, alternatively, making 5-amino-2,4-difluoro-3-Q1-benzoic acid as in step (iv), then treating the 5-amino-2,4-difluoro-3-Q1-benzoic acid with an alkali metal nitrate in acid, and then with a heavy metal cyanide to give the cyano Q2; and (vi) incorporating an acyl Q2 by treating the 2,4-difluoro-3-Q1-benzoic acid with an acylating agent to give the acyl Q2.

9. The process of claim 8 wherein step (e) is selected from the group consisting of:

(i) incorporating a halo Q3 by treating the 2,4-difluoro-3-Q1-5-Q2-benzoic acid with $Z_2$ under acidic conditions, where Z is halo;

(ii) incorporating a hydroxy Q3 or alkoxy Q3 by making 6-bromo-2,4-difluoro-3-Q1-5-Q2-benzoic acid as in step (i); then treating the 6-bromo-2,4-difluoro-3-Q1-5-Q2-benzoic acid with n-butyllithium, then with lithium t-butyl hydroperoxide to give the hydroxy Q3; and optionally alkylating the hydroxy Q3 to the alkoxy Q3;

(iii) incorporating an alkanyl, alkenyl or aryl Q3 by making 6-bromo-2,4-difluoro-3-Q1-5-Q2-benzoic acid as in step (i); then treating the 6-bromo-2,4-difluoro-3-Q1-5-Q2-benzoic acid with n-butyllithium, then with alkanyl, alkenyl or aryl iodide to give the alkanyl, alkenyl or aryl Q3; or, alternatively, treating the 6-bromo-2,4-difluoro-3-Q1-5-Q2-benzoic acid with R-trialkanyltin, where R is alkanyl, alkenyl or aryl in the presence of catalyst to give the alkanyl, alkenyl or aryl Q3;

(iv) incorporating a nitro Q3 or amino Q3 by treating the 2,4-difluoro-3-Q1-5-Q2-benzoic acid with activated nitric acid to give the nitro Q3, and optionally reducing the nitro Q3 to the amino Q3;

(v) incorporating a cyano Q3 by making 6-bromo-2,4-difluoro-3-Q1-5-Q2-benzoic acid as in step (i), then treating the 6-bromo-2,4-difluoro-3-Q1-5-Q2-benzoic acid with a heavy metal cyanide to give the cyano Q3; or, alternatively, making 6-anino-2,4-difluoro-3-Q1-5-Q2-benzoic acid as in step (iv), then treating the 6-amino-2,4-difluoro-3-Q1-5-Q2-benzoic acid with an alkali metal nitrate in acid, and then with a heavy metal cyanide to give the cyano Q3; and (vi) incorporating an acyl Q3 by treating the 2,4-difluoro-3-Q1-benzoic acid with an acylating agent to give the acyl Q3.

10. The process of claim 7 wherein step (d) comprises: treating the 2,4-difluoro-3-Q1-benzoic acid with thionyl chloride, then treating with 2-amino-2-methyl-1-propanol, then cyclizing by treating with thionyl chloride, then treating with lithium diisopropylamide, then treating with an electrophilic reagent which provides Q3 or a functional moiety which is then transformed to Q3, then hydrolyzing, producing 6-Q3-2,4-difluoro-3-Q1-benzoic acid.

11. The process of claim 10 wherein the electrophilic reagent is selected from the group consisting of RI, RBr, ROS($O_2$)OR, ROSO$_2$R', FClO$_3$, (CCl$_3$)$_2$, (CCl$_3$)$_2$CO, N-chlorosuccinimide, Br$_2$, (CH$_2$Br)$_2$, I$_2$, (CH$_2$I)$_2$, O$_2$, tBuOOH, $BR_3/H_2O_2$, $(MeO)_3B/H_2O_2$, RSSR, DMF, HC(O)$NR_2$, $CO_2$, ClCOOR, HC(O)R, $R_2CO$, transition metal/ArI, transition metal/RCH=CHI, wherein R is lower alkanyl and Ar is aryl.

12. The process of claim 7 wherein Q1 is selected from the group consisting of alkanyl, alkenyl, aryl, halo, hydroxy, alkoxy, acyloxy, alkanylthio, formyl, carboxyl, and carboxylate; Q2 is selected from the group consisting of hydrogen, iodo, bromo, chloro, hydroxy, alkoxy, nitro, amino, alkyl, cyano, and acyl; and Q3 is selected from the group consisting of hydrogen, halo, hydroxy, alkoxy, amino, alkyl, alkanylthio, formyl, carboxyl, carboxylate, and aryl.

13. The process of claim 12 wherein Q1 is selected from the group consisting of alkanyl, halo, hydroxy, alkoxy, acyloxy, alkanylthio, formyl, carboxyl, and carboxylate; Q2 is selected from the group consisting of hydrogen, bromo, chloro, hydroxy, alkoxy, amino, alkyl, and cyano; and Q3 is selected from the group consisting of hydrogen, halo, hydroxy, lower alkanoxy, and lower alkanyl.

14. The process of any of claims 7, 8, 9, 11 and 13, wherein step (b) comprises treating the 1-bromo-2,4-difluoro-3-Q1-benzene with a strong base; then treating with carbon dioxide.

* * * * *